Figure 1:
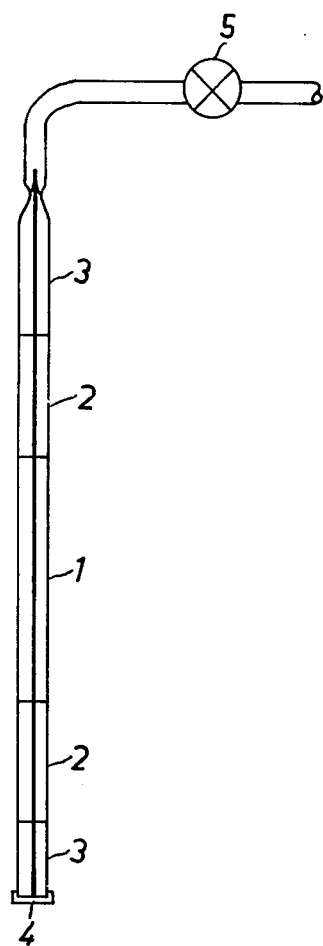

United States Patent [19]

Hallberg et al.

[11] 4,211,615

[45] Jul. 8, 1980

[54] PROCESS AND A MEASURING CELL FOR THE COULOMETRIC DETERMINATION OF THE CONTENT OF A COMPONENT DISSOLVED IN WATER

[76] Inventors: Rolf O. Hallberg, Skolvagen 11A, 135 00 Tyreso; Carl H. M. Lindstrom, Sandelsgatan 10, 115 33 Stockholm; Hakan Westerberg, Paskvagen 32, 421 53 Vastra Frolunda, all of Sweden

[21] Appl. No.: 35,383

[22] Filed: May 2, 1979

[51] Int. Cl.$^2$ .............................................. G01N 27/42
[52] U.S. Cl. ................................. 204/1 T; 204/195 R
[58] Field of Search .................. 204/195 R, 1 R, 1 M, 204/195 T

[56] References Cited

U.S. PATENT DOCUMENTS

| | | | |
|---|---|---|---|
| 3,498,888 | 3/1970 | Johansson | 204/1 T |
| 3,761,376 | 9/1973 | Barstow et al. | 204/195 R |
| 3,950,237 | 4/1976 | Arakawa et al. | 204/195 T |

*Primary Examiner*—G. L. Kaplan
*Attorney, Agent, or Firm*—Irons and Sears

[57] ABSTRACT

A process for the coulometric determination of the content of a component dissolved in water, e.g. oxygen gas in sea-water, and a coulometer cell for carrying out said process. The cell consists of an elongated, central measuring cell (1) and two auxiliary cells (2) which are directly connected to each end of the measuring cell (1). Electrolysis is performed simultaneously in the measuring cell (1) and the auxiliary cells (2) under such conditions that the concentration of the dissolved component will decrease at the same rate in all three cell elements.

3 Claims, 4 Drawing Figures

FIG. 2
FIG. 3
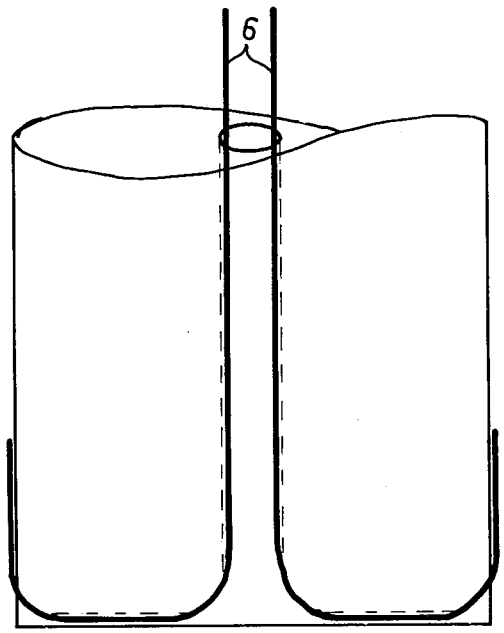
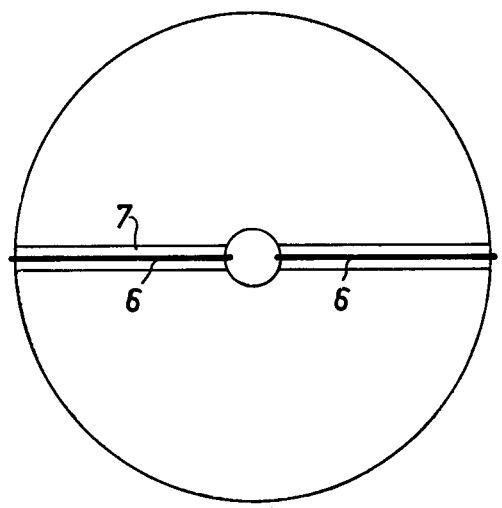
FIG. 4
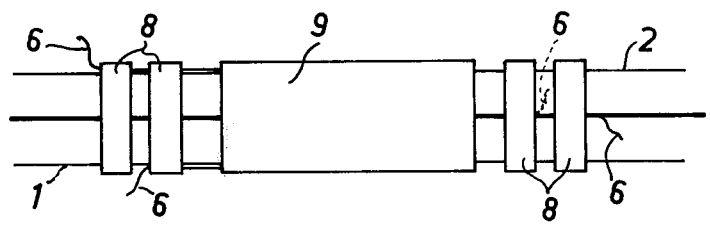

PROCESS AND A MEASURING CELL FOR THE COULOMETRIC DETERMINATION OF THE CONTENT OF A COMPONENT DISSOLVED IN WATER

The present invention relates to a process for the coulometric determination of the content of components dissolved in water, such as gases, e.g. oxygen gas in sea-water, and ions, e.g. iron ions, and a measuring cell for carrying out the process.

Various titrimetric methods can be used for the determination of the content of components dissolved in water. A number of electrochemical measuring devices are available for measurements in situ. These devices are often based upon a galvanometric or polarographic principle. This means that the measuring signal is proportional to the flow of the component towards an electrode surface. At constant diffusion conditions said flow is proportional to the area of the electrode and to the chemical potential, of the dissolved component. The area of the electrode will vary due to precipitation on and contamination of the electrode surface. As a result thereof this type of instrument exhibits an unsatisfactory precision and long term stability. When measuring dissolved gases salinity and temperature must be determined in addition to the partial pressure of the gas if the concentration is to be calculated.

Also coulometric methods have been previously used; not very successfully, however.

According to the invention an improved coulometric measuring method has been developed, in which method a specific three-part coulometer cell is used.

Thus, the invention relates to a process for the coulometric determination of the content of a component dissolved in water, in which process a definite constant voltage is applied across the electrodes of a coulometer cell filled with a water sample, said constant voltage being maintained for a period of time sufficient for a complete reaction of the dissolved component in a desired electrode reaction, the quantity of electricity passing through the cell being measured by integration, and the content of the dissolved component being calculated on the basis of said integration. The process is characterized by employing an elongated three-part coulometer cell composed of a central measuring cell and two auxiliary cells which are directly connected to each end of the measuring cell, and by performing electrolysis simultaneously in the measuring cell and the auxiliary cells under such conditions that the concentration of the dissolved component will decrease at the same rate in all three cell elements, two such electrolyses being performed with the same integration time in order to correct for temperature and salt content dependence and for charging of the electric double layer.

The coulometer cell used in this process is characterized in that it consists of an elongated central measuring cell which has both of its ends directly connected each to one of two elongated auxiliary cells, each of the measuring and auxiliary cells being provided with an anode and a cathode in the form of electrically conducting wires, said wires being parallel inter se and extending in the longitudinal direction of the respective cell elements.

A specific embodiment of the invention is described below, viz. the determination of the content of oxygen gas dissolved in sea-water. However, the invention is not limited to said embodiment but can be used also for the determination of other reactive gases dissolved in water, such as hydrogen sulphide and sulphur dioxide, and ions, such as iron and manganese ions, etc. In each particular case the electrode materials and the voltage applied are chosen in such a manner that the component to be analyzed will participate in a definite electrode reaction which shall be the dominating reaction at the electrode in question.

The principle utilized in the determination of oxygen in sea-water is based upon the fact that in sea-water the reduction of oxygen is the electrode reaction of quantitative importance which has the lowest activation potential at a platinum cathode. By a suitable choice of anode and potential difference of the cell essentially all current through the cell is a function of the reduction of oxygen and is limited only by the supply of oxygen for the cathode reaction. In a defined volume the total number of electrons which can pass through the cell is quantitatively determined by the amount of dissolved oxygen gas in the volume according to Faraday's law.

The following is the dominating cathode reaction:

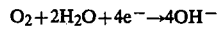

$$O_2 + 2H_2O + 4e^- \rightarrow 4OH^-$$

A silver-plated platinum wire is suitably used as the anode, the anode reaction being the following:

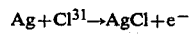

$$Ag + Cl^{31} \rightarrow AgCl + e^-$$

The dimensions of the electrolysis cell are determined i.a. by the conditions that the electrolysis time should be moderate (normally maximum 15 minutes) and that the current through the cell should be measurable with a reasonable precision and simplicity. Said conditions lead to a very long and narrow cell in the form of a tube with the electrodes extending in the axial direction. Suitable cell dimensions are the following: diameter 0.3–0.4 mm; length 100–200 mm.

It is difficult mechanically to close and open such a small volume with accuracy, especially as the volume between the cell and the surrounding liquid should be of the same order of magnitude as the cell volume to facilitate the rinsing between the measurements.

The solution according to the invention is to use a measuring cell open in both ends but connected to identical electrolysis cells (auxiliary cells) which are switched in at the same time as the measuring cell. This means that the oxygen concentration in the adjacent auxiliary cells is essentially the same as that in the measuring cell during the whole electrolysis, so no diffusion of oxygen into the measuring volume will take place. The liquid column through the measuring and auxiliary cells is kept immovable during the measurement by using a pump not permitting any passage of liquid. Small liquid movements due to a moderate leakage or due to temperature expansion do not affect the measuring result since the liquid entering into the cell has the same oxygen concentration as the liquid being replaced. The advantage of the design according to the invention is that the measuring volume is well defined since longitudinal advection and diffusion of oxygen have been eliminated.

The invention will be described below referring to the drawings in which

FIG. 1 shows the fundamental construction of the coulometer cell; FIGS. 2 and 3 show the extension of the electrode wires; and FIG. 4 illustrates the joining of a measuring cell with an auxiliary cell.

The fundamental construction of the cell is shown in FIG. 1. The cell consists of a central measuring cell 1 and two auxiliary cells 2 on each side of the measuring cell. The measuring cell as well as the auxiliary cells consist of open tube segments (capillary tubes) interconnected to each other. The capillary tubes are normally glass tubes, e.g. of Pyrex glass. If the length of the measuring cell is 100 mm, the length of each auxiliary cell may be e.g. 50 mm. The auxiliary cells 2 are connected to outer tube segments 3. The tube segment 3 in the intake end is connected to a particle filter 4, possibly via a plastics hose. The tube segment 3 in the other end is, via a plastics hose, connected to a pump 5, preferably a peristaltic pump.

FIGS. 2 and 3 show how threadlike electrodes 6 are arranged in the longitudinal direction of a measuring cell or auxiliary cell and, in the ends of the capillary tube, are located in grooves 7 between the inner surface and the outer surface of the capillary tube.

In the determination of oxygen the cathode consists of a fine platinum wire, and the anode consists of a similar platinum wire coated with a silver layer. If the inner diameter of the capillary tube is e.g. 0.4 mm the diameter of the platinum wires may be 0.05 mm. The thickness of the anode silver layer may be 0.01 mm.

The wires are applied in the following way. Each wire is passed through the capillary tube, one end of the wire is folded over one end of the tube in said groove, and the wire end is fixed on the outer side of the tube, e.g. by means of an adhesive and shrinkable plastics hose 8 (see FIG. 4). The wire is stretched by hand along the inner side of the tube, and the other wire end is fixed in the same way as the first end. The two wires in each capillary tube are applied diametrically opposite to each other.

FIG. 4 illustrates the joining of a measuring cell 1 and an auxiliary cell 2. The auxiliary cell is turned 90° in relation to the measuring cell so that the electrodes 6 of the two cells will not contact each other. Some silicon rubber is applied to the ends of the tube segments, the ends are then pressed against each other and shrinkable plastics hose 9 is applied to hold said ends together. Each auxiliary cell 2 is joined with an outer tube segment 3 in the same way.

The two ends of each electrode wire 6 are connected in any suitable way to a connection wire. The various connection wires are brought together in a screened cable. The two auxiliary cells are connected electrically. The cell assembly is applied in a plexiglass housing and all joints and solders are casted into an adhesive, e.g. of epoxy type.

Before the measurement water is sucked into the measuring cell by means of the pump 5. The flow velocity is controlled in such a manner that the depression in the measuring cell will not be so great that gas bubbles are formed. Furthermore, the rinsing of the cell must be performed for a period of time sufficient for the replacement of the whole liquid volume of the measuring cell (thus, also the liquid nearest the cell wall) by new test liquid. After stopping the pump the electrolysis can be started.

It is important that the voltage applied is maintained constant during the whole electrolysis time and this can be accomplished by means of two operational amplifiers, one for the measuring cell and one for the two auxiliary cells. The reference voltage is obtained via a voltage divider from the stabilized supply voltage. During each moment of the electrolysis the oxygen concentration in the auxiliary cells will be equal to the oxygen concentration in the measuring cell.

At the time t=0 a constant voltage is applied across the electrodes. After the time t the charge Q' has passed through the cell. Said charge can be divided in the following components:

(1) The Faraday charge $Q'_F$ which is related to the reaction $$O_2 + 2H_2O + 4e^- \rightarrow 4OH^-$$

(2) The charge $Q'_S$ deriving from trace amounts of substances reacting at the same overpotential as oxygen or at a lower potential. The quantitatively dominating reactions in sea-water are probably the following:

$$Cu^{2+} + 2e^- \rightarrow Cu$$

$$SeO_4^{2-} + H_2O + 2e^- \rightarrow SeO_3^{2-} + 2OH^-$$

$$BiCl_4^- + 3e^- \rightarrow Bi + 4Cl^-$$

(3) Slow reactions having an activating potential higher than the cell voltage used give a charge $Q'_o$.
(4) The charge $Q'_D$ necessary for building up the electrical double layer at the working electrode.

The current associated with the charges $Q'_F$, $Q'_S$ and $Q'_D$ will decrease exponentially with the time, so said charges approach constant values $Q_F$, $Q_S$ and $Q_D$ when t approaches infinity. On the other hand, the reactions giving the charge $Q'_o$ are slow and the concentration change of the reacting substances may be neglected. We have the following approximate relationships:

$$\frac{\partial Q'_F}{\partial t} \approx \frac{4F[O_2]V}{\tau_F} \cdot e^{-\frac{t}{\tau_F}}$$

$$\frac{\partial Q'_S}{\partial t} \approx \frac{F\{2[Cu^{2+}] + 2[SeO_4^{2-}] + \ldots\}V}{\tau_S} \cdot e^{-\frac{t}{\tau_S}}$$

$$\frac{\partial Q'_D}{\partial t} \approx \frac{C_D A E}{\tau_D} \cdot e^{-\frac{t}{\tau_D}}$$

$$\frac{\partial Q'_o}{\partial t} \approx K_o$$

wherein
F = Avogadro number
V = the cell volume
A = the area of the working electrode
[X] = the molarity of X
E' = the electrode potential in relation to electrocapillary maximum.

If the total integration time T is great as compared to $\tau_F$, $\tau_S$ and $\tau_D$ we have the following relationship:

$$Q = \int_0^T i\,dt = Q_F + Q_S + Q_D + T \cdot K_o$$

The charge $Q_F$ is a measure of the oxygen concentration to be determined. $Q_D$ and $T k_o$ are probably salt and temperature dependent and proportional to the effective electrode area. According to the invention said terms are determined by a second electrolysis of the same sample with the same integration time. The charge will then be:

$$Q^* = Q_D + TK_o$$

Thus: $Q - Q^* = Q_F + Q_S$

The magnitude of $Q_S$ depends upon the content of the substances being capable of reacting at the working electrode. We have the following ratio:

$$\frac{Q_S}{Q_F} \quad \frac{[Cu^{2+}] + [SeO_4^{2-}] + \ldots}{[O_2]}$$

In sea-water saturated with oxygen said ratio is about $10^{-4}$; furthermore, the concentrations of the ions are proportional to the salinity S.

By means of the double integration the following calibration equation is obtained:

$$\Delta Q = Q - Q^* = K[O_2] + kS$$

This equation is not temperature dependent, and $K \leq k$.

The integration is carried out in the following way. The anode of the measuring cell is connected to an operational amplifier which functions as a current-to-voltage converter and is provided with a booster amplifier so that the current surge passing through the cell and the current-to-voltage converter initially shall not affect the input parameters of the converter. The voltage is converted by means of a voltage-to-frequency converter to a pulse train with voltage proportional frequency which is counted in an up/down counter. In the first integration the frequency is counted up, and in the second integration the frequency is counted down from the first value.

When determining oxygen in sea-water by means of the inventive process the accuracy attained is as good as that attained in conventional Winkler titration.

We claim:

1. A process for the coulometric determination of the content of a component dissolved in water, in which process a definite constant voltage is applied across the electrodes of a coulometer cell filled with a water sample, said constant voltage being maintained for a period of time sufficient for a complete reaction of the dissolved component in a desired electrode reaction, the quantity of electricity passing through the cell being measured by integration, and the content of the dissolved component being calculated on the basis of said integration, characterized by employing an elongated three-part coulometer cell composed of a central measuring cell and two auxiliary cells which are directly connected to each end of the measuring cell, and by performing electrolysis simultaneously in the measuring cell and the auxiliary cells under such conditions that the concentration of the dissolved component will decrease at the same rate in all three cell elements, two such electrolyses being performed with the same integration time in order to correct for temperature and salt content dependence and for charging of the electric double layer.

2. A coulometer cell for the coulometric determination of the content of a component dissolved in water, characterized in that it consists of an elongated central measuring cell which has both of its ends directly connected each to one of two elongated auxiliary cells, each of the measuring and auxiliary cells being provided with an anode and a cathode in the form of electrically conducting wires, said wires being parallel inter se and extending in the longitudinal direction of the respective cell elements.

3. A cell according to claim 2, characterized in that the cathode wires consist of platinum wires and that the anode wires consist of silver-plated platinum wires.

* * * * *